United States Patent [19]

Bender et al.

[11] Patent Number: 5,327,225
[45] Date of Patent: Jul. 5, 1994

[54] SURFACE PLASMON RESONANCE SENSOR

[75] Inventors: William J. H. Bender, Lancaster, Pa.; Raymond E. Dessy, Blacksburg, Va.

[73] Assignee: The Center for Innovative Technology, Herndon, Va.

[21] Appl. No.: 10,267

[22] Filed: Jan. 28, 1993

[51] Int. Cl.⁵ .............................. G01N 21/55
[52] U.S. Cl. ..................... 356/445; 356/317; 356/318; 250/306; 250/307; 422/82.05; 422/82.09; 422/66; 435/808; 436/515; 436/516
[58] Field of Search ............ 356/317, 318, 445; 250/306, 307; 422/82.05, 82.09, 66; 435/808; 436/515, 516

[56] References Cited

U.S. PATENT DOCUMENTS

| | | | |
|---|---|---|---|
| 5,023,053 | 6/1991 | Finlan | 356/318 |
| 5,047,213 | 9/1991 | Finlan et al. | 356/318 |
| 5,047,633 | 9/1991 | Finlan et al. | 250/306 |

Primary Examiner—Richard A. Rosenberger
Assistant Examiner—LaCharles P. Keesee, II
Attorney, Agent, or Firm—Whitham, Curtis & Whitham

[57] ABSTRACT

An optical fiber surface plasmon resonance (SPR) sensor includes both a metal layer and an overlay or underlay material on its surface. Existing fiber based SPR devices are inherently incapable of monitoring aqueous systems which have a refractive index ranging between 1.33 and 1.35, and existing prism based SPR sensors have proved too cumbersome for online chemical and biochemical analyses. Inclusion of the overlay or underlay material on the SPR sensor allows monitoring media with a refractive index from 1.00 to the 1.39 barrier and above. Hence, the SPR sensor allows monitoring important biochemical and chemical aqueous processes where the media typically have a refractive index between 1.33 and 1.35. In operation, samples are simply applied to the sensing region of the SPR sensor where the metal layer and overlay or underlay materials are coated, introducing a polarized beam of light into the optical fiber, and detecting surface plasmon resonance. The optical fiber can be positioned in a flow cell for on line operations where media are simply moved past the sensing region of the SPR sensor or can be part of a dip stick which is used for batch processes. The SPR sensor has particular utility in monitoring biochemical (antigen-antibody) reactions, detecting corrosion of metal surfaces, and identifying chemical products in an HPLC effluent.

22 Claims, 11 Drawing Sheets

RAY TRACE MODEL (LARGE DIAMETERS)

MODE MODEL (SMALL DIAMETERS)

SURFACE PLASMON RESONANCE SENSOR

BACKGROUND OF THE INVENTION

1. Field of the Invention

This invention is generally related to surface plasmon resonance (SPR) based devices. More particularly, the present invention is related to a surface modified optical fiber sensor of a wider refractive index range than heretofore possible.

2. Description of the Prior Art

Surface plasmon resonance is the oscillation of the plasma of free electrons which exists at a metal boundary. These oscillations are affected by the refractive index of the material adjacent the metal surface. Surface plasmon resonance may be achieved by using the evanescent wave which is generated when a p-polarized light beam is totally internally reflected at the boundary of a medium, e.g., glass, which has a high dielectric constant. A paper describing the technique has been published under the title "Surface plasmon resonance for gas detection and biosensing" by Lieberg, Nylander and Lundstrom in Sensors and Actuators, Vol. 4, page 299.

Illustrated in FIG. 1 of the accompanying drawings is a diagram of the equipment described in the Liegerg paper. A beam 1 of light is directed from a laser source (not shown) onto an internal surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs, the refractive index of the film 6 will change owing to the increased size of the antibody molecules, and this change can be detected and measured using surface plasmon resonance techniques.

Surface plasmon resonance can be experimentally observed by varying the angle of the incident beam 1 and monitoring the intensity of the internally reflected beam 4. At a certain angle of incidence, the parallel component of the light momentum will match with the dispersion for surface plasmons at the opposite surface 8 of the metal film 5. Provided that the thickness of metal film 5 is chosen correctly, there will be an electromagnetic coupling between the glass/metal interface at surface 2 and the metal/antibody interface at surface 8 which results in surface plasmon resonance, and thus an attenuation in the reflected beam 4 at that particular angle of incidence. Thus, as the angle of incidence of beam 1 is varied, surface plasmon resonance is observed as a sharp dip in the intensity of the internally reflected beam 4 at a particular angle of incidence. The angle of incidence at which resonance occurs is affected by the refractive index of the material against the metal film 5, i.e. the antibody film 6, and the angle of incidence corresponding to resonance is thus a direct measure of the state of the reaction between the antibody and the antigen. Increased sensitivity can be obtained by choosing an angle of incidence half way down the reflectance dip curve where the response is substantially linear at the beginning of the antibody/antigen reaction, and then maintaining that angle of incidence fixed and observing changes in the intensity of the reflected beam 4 with time.

As the angle of incidence is changed, either by moving the light source or rotating the glass body, or both, the point on surface 2 at which the incoming beam 1 is incident moves. Because of inevitable variations in the metal film 5 and the antibody film 6, the angle of incidence at which resonance occurs changes as the point of incidence of incoming beam 1 moves, which, in turn, introduces a further variable factor into the measurement and thus makes comparison between the initial unbound state and the bound state of the antibody film 6 less accurate.

FIG. 2 shows a surface plasmon resonance sensor where the glass body is a prism 13 and a thin film 15 of metal is applied to its undersurface. Light 11 from a laser source is incident on the prism 13 where it is refracted at point 19 before entering the prism 13. The internally reflected beam 14 is likewise refracted at point 20 upon exiting from the prism 13. U.S. Pat. Nos. 5,064,619, 5,055,265, 5,047,633, 5,047,213, 5,035,863, 5,023,053, and 4,997,278 to Finlan, and U.S. Pat. No. 4,889,427 to VanVeen et al. describe prism-based SPR sensors.

SUMMARY OF THE INVENTION

An object of this invention is to provide an optical fiber SPR sensor.

Another object of this invention is to provide an SPR sensor which can detect changes in the refractive index of a chemical or biochemical sample.

Another object of the invention is to provide a tool for assaying chemical or biological reactions without the use of specific markers.

It is yet another object of the invention to provide a quadruple layer SPR-based sensor.

A further object of the invention is to provide means for monitoring corrosion processes of metallic overlay materials and for analytical process control.

An additional object of this invention is to provide an SPR sensor of much wider refractive index range than heretofore known or described.

It is yet another object of the invention to provide dispersion equations determinative of conditions necessary to achieve surface plasmon resonance.

According to the invention, an SPR sensor includes an optical fiber with an electromagnetic radiation source (laser) and a detector connected to opposite ends of the fiber and both a metal layer and an overlay or underlay material coated on its surface. The overlay or underlay material permits analyzing samples of a much wider refractive index range than previously possible, and allows the optical fiber SPR sensor to be used in biochemical and chemical applications. In operation, a sample is brought into contact with the optical fiber SPR sensor. The overlay or underlay material on the sensor can include a bound solid-phase for antigen-antibody reactions or the like. The evanescent field portion of the beam of electromagnetic radiation incident upon the metal layer generates surface plasmon resonance which changes as a function of the refractive index of the sample. The effective index of the surface plasmon generated is dependent on the thickness and refractive index of the metal layer and the overlay or underlay material, as well as the refractive index of the sample. Changes in the surface plasmon resonance due to an interaction between the sample and a solid-phase on the overlay or underlay material, or changes in the refractive index of the sample due to a chemical reaction, etc., are detected and used for identifying the presence of an antigen or antibody, process controls, and the like.

BRIEF DESCRIPTION OF THE DRAWINGS

The foregoing and other objects, features and many of the attendant advantages of the invention will be better understood upon a reading of the following detailed description when considered in connection with the accompanying drawings, wherein.

DETAILED DESCRIPTION OF THE INVENTION

Surface plasmon is a transverse magnetic (TM) electromagnetic wave guided by a thin metal film surrounded by dielectric material. The plasmon is a surface effect which causes electron density fluctuations at the interface between the metal and the dielectric. The generation of surface plasmons occurs when energy contained in an evanescent field is coupled into the plasmon mode on the metal film. The amount of coupling is extremely sensitive to the refractive indices of the dielectric materials on both sides of the metal film. If one of the dielectric layers consists of a chemical sample, changes in this sample's refractive index can be monitored by measuring changes in the evanescent field to plasmon coupling efficiency.

SPR was initially used as a probe to investigate metal surfaces, then later as the basis for chemical and biochemical sensor devices. Initial experiments involved the use of a prism onto which the metal film was deposited. The reflection from the prism/metal interface of a p-polarized laser at angles less than the critical angle ($\theta_c$) was monitored with a photodetector. When the angle of incidence of the laser beam is scanned from a highly grazing angle up to near $\theta_c$, a sharp minimum in reflectivity is seen at a very discrete angle. At this angle the wave vector of the laser beam in the prism matches the wave vector of the plasmon, and energy from the laser is coupled to the plasmon via the evanescent field at the reflection point. The position of the minimum is strongly dependent on the refractive index of any material (sample) disposed onto the surface of the metal. An increase in sample refractive index leads to an increase in the angle of minimum reflectivity.

SPR has been utilized in the fiber optic communications field as the basis for an in-line, all-fiber polarization device.

Chemical reactions can be monitored using SPR with optical fibers clad with metal films; however, only samples whose refractive indices are larger than approximately 1.39 can be monitored. This limitation is inherent to optical fibers because of the limited range of cladding indices available. The dispersion equation is strongly dependent on cladding index. Most chemical and biochemical applications require monitoring reactions where the refractive index of the sample media ranges between 1.33 and 1.35. Hence, a modification of the fiber is necessary in order to monitor that refractive index range.

Figure 1:
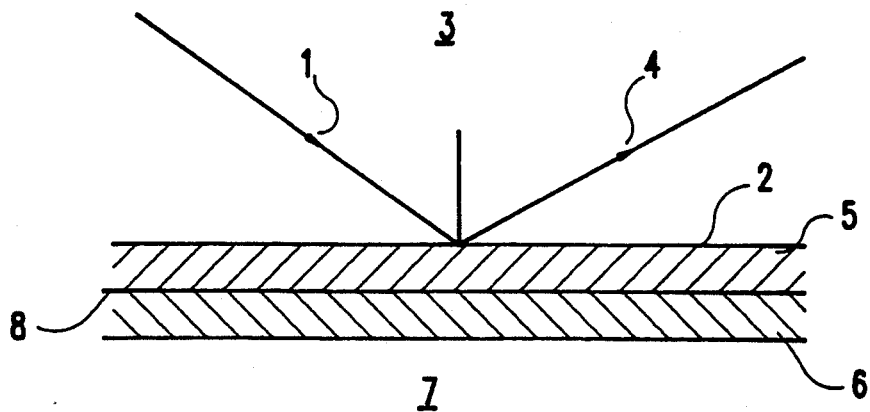
FIG. 1 is a schematic drawing of a prior art SPR sensor.
Figure 2:
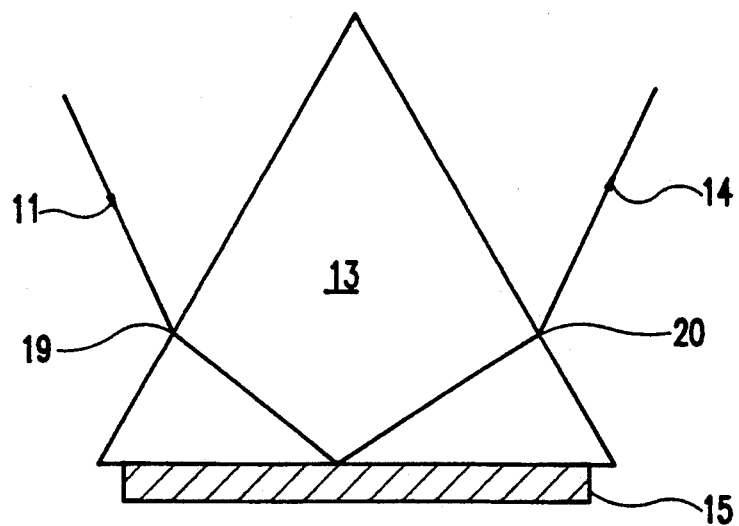
FIG. 2 is a schematic drawing of a prism based SPR sensor.
Figure 3A:
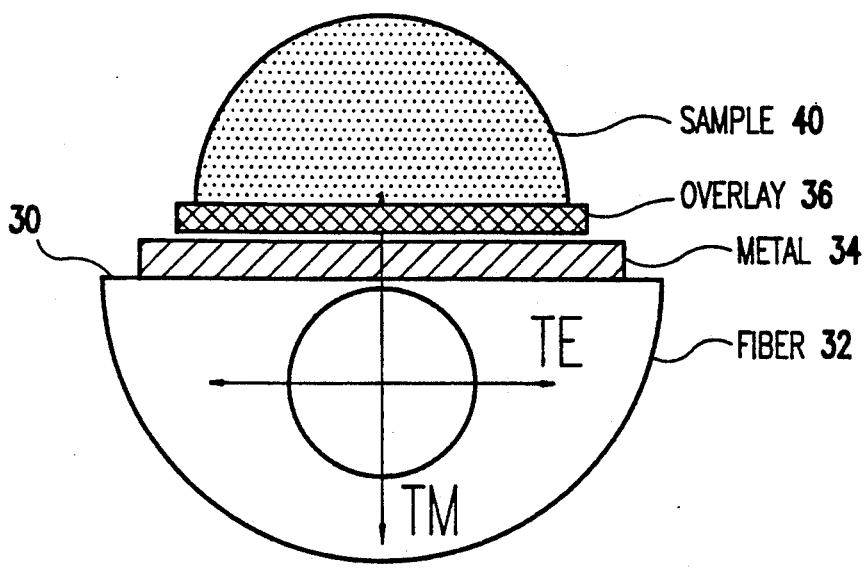
FIGS. 3a and 3b are cross-sectional views of optical fiber SPR sensors of the present invention which include a metal film and an overlay or underlay material, respectively, coated on the surface of the optical fiber.
Figure 3B:
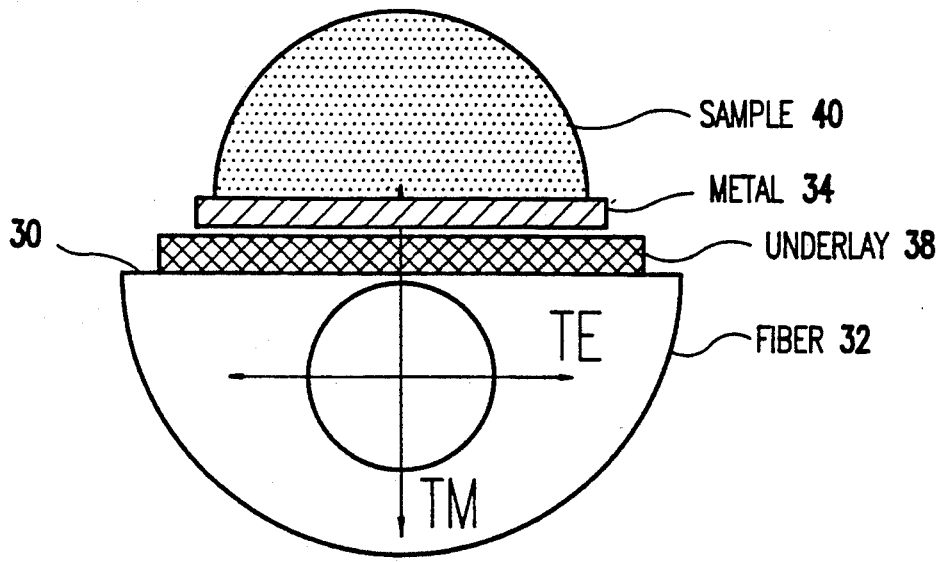

FIGS. 3a and 3b show the construction of optical fiber SPR sensors according to the present invention. The polished surface 30 of an optical fiber 32 includes both a conductive (metal) film 34 and an overlay 36 or underlay 38 material coated thereon. In order to produce a fiber based SPR device, a dispersion equation must be generated to describe the conditions necessary to achieve the resonance condition, and the device must be constructed to monitor the refractive index range of the target application. In a preferred embodiment of his invention, the metal film 34 and overlay 36 or underlay 38 materials are chosen to monitor chemical or biochemical reactions in aqueous samples 40.

EXAMPLE 1—SENSOR FABRICATION

The optical fiber SPR sensors of the present invention can be fabricated by a number of different methods. In a technique performed by the inventors, a section of the fiber 32 is bonded to a curved aluminum polishing substrate. The surface of the fiber 32 is then polished and the polishing procedure is controlled by monitoring laser throughput in the fiber. When the polishing reaches the evanescent field, the laser intensity starts to decline and the polishing procedure is terminated. The polished surface 30 of the fiber 32 is then coated with metal 34 and overlay 36 or underlay 38 material by standard processes, including vacuum vapor deposition, electron beam deposition, sputtering, chemical vapor deposition, and the like. Preferably, the fiber 32 is placed on the target of the deposition unit and deposition is carried out at reduced pressure. The coating thickness is controlled with a quartz crystal oscillator or other suitable thickness monitor. The overlay 36 or underlay 38 material should have a high refractive index, so only a thin layer need be deposited. In addition, the overlay 36 or underlay 38 material should have a low melting point to promote vapor deposition, and it should be insoluble in water if the SPR sensor is to be used for aqueous analysis.

In experiments discussed below, an overlay 36 material was used in the SPR sensor and the overlay 36 was silicon monoxide. However, it should be understood the overlay 36 could comprise organic or inorganic layers, polymeric layers, metals or semiconductive materials, or other dielectric and glass materials. In addition, the overlay 36 or underlay 38 material could be comprised of two or more materials. A number of materials will be suitable for use as the metal film 34, including silver, gold, aluminum, chromium, and alloys thereof. Semiconductors such as silicon or germanium, or conductive polymers might be substituted for the metal film. In the experiments described below, the metal film was silver. The thickness and refractive index of the metal film 34 and overlay 36 or underlay 38 material are important factors in the performance of the optical fiber SPR sensors, and FIGS. 3a and 3b show that the order in which they are coated on the fiber 32 can be reversed; however, using an overlay 36 material has certain advantages. Specifically, the overlay 36 could include a solid-phase with bound antibodies or antigens that are brought into intimate contact with an analyte of interest in the sample 40. The overlay 36 could also be porous to increase the surface area for antibody-antigen interactions or to allow corrosive agents to contact the metal film.

FIGS. 3a and 3b show that the metal film 34 and overlay 36 or underlay 38 coatings on the surface 30 of the fiber allow the evanescent field present in the fiber 32 to penetrate the coatings. This can be accomplished by several methods including: polishing the fiber's 32 surface to within the evanescent field and applying the coatings to the polished section as described above; using an unclad fiber and applying the coatings directly to the core (the application of metal layers directly to the core tends to attenuate guided modes); using a fiber with a very thin cladding (e.g., less than a few microns thick) and applying the coatings directly to the cladding; or substituting a planar optical wave guide for the optical fiber.

The plasmon, being a surface effect, is sensitive to only a few to several hundred nanometers of material above the metal surface. Consequently, the thickness of the plasmon sampling region of the device (e.g., the thickness of the metal film 34 plus the overlay 36 or underlay 38) is only a few to several hundred nanometers. If the overlay 36 or underlay 38 is comprised a highly refractive material, the 'net' refractive index of the plasmon sampling region (overlay or underlay refractive index plus sample refractive index) can be adjusted to a level that allows monitoring samples 40 by surface plasmon resonance with an optical fiber-based SPR device. Hence, the optical fiber-based SPR sensors of the present invention are capable of monitoring samples 40 with refractive indices from 1.00 up to and beyond the 1.39 limit inherent in an optical fiber SPR sensor with no overlay 36 or underlay 38 material. The exact index monitored is determined by the refractive index and thickness of the overlay 36 or underlay 38.

EXAMPLE 2—SPR SENSOR PARAMETERS

It is noted that only for simplicity of calculations, the cladding and sample layers are assumed to be semi-infinite and the polished fiber is assumed to approximate a planar waveguide. This is shown schematically in FIG. 4. These assumptions simplify the derivation of the dispersion equation and are validated by the work of Johnstone et al., *J. Light Technol.* 8:538 (1990). Since the plasmon is a transverse magnetic (TM) effect, only the $H_y$ and $E_z$ fields need to be considered. Starting with Maxwell's equations, the one-dimensional waveguide equation for the y-component of the magnetic field in a TM wave can be derived by the following equations (Marcuse, 1973, Theory of Dielectric Optical Waveguides, Academic Press, N.Y. Chapter 1):

$$\delta^2 H_y / \delta x^2 + (n^2 k^2 - \beta^2) H_y = 0$$

and the z-component of the electric field is $$E_z = (-i/n^2 \omega E_0) \delta H_y / \delta x$$

For the above equations, n is the refractive index, $k = 2\pi/\lambda$, and $\beta$ is the propogation constant of the mode in the fiber. A solution to the waveguide equation is expressed in equation 3.

$$H_y = A e^{ix(n^2 k^2 - \beta^2)^{\frac{1}{2}}} + B e^{-ix(n^2 k^2 - \beta^2)^{\frac{1}{2}}}$$

and therefore $E_z$ given in equation 2 can be written according to equation 4.

$$E_z = (-i/n^2 \omega E_0) \{ A i (n^2 k^2 - \beta^2)^{\frac{1}{2}} \cdot e^{ix(n^2 k^2 - \beta^2)^{\frac{1}{2}}} - B i (n^2 k^2 - \beta^2)^{178} \cdot e^{-ix(n^2 k^2 - \beta^2)^{\frac{1}{2}}} \}$$

A and B are constants obtained from the solution of the differential equation and will be discussed later.

Figure 4:
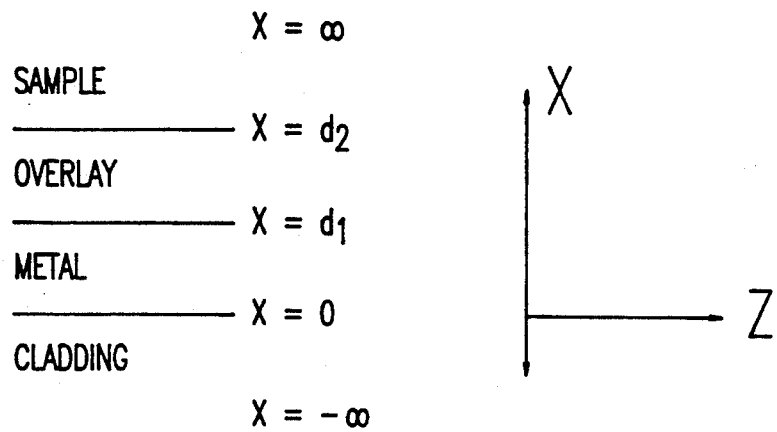
FIG. 4 is a schematic drawing of a theoretical quadruple layer arrangement for the optical fiber SPR sensors of the present invention.

The four layers in the sensor configuration (cladding, metal, overlay, and sample) shown in FIG. 4 each have a different refractive index and therefore produce a different expression for $H_y$ and $E_z$ from equations 3 and 4 above. Equations 5 and 6 present the different equations for $H_y$ and $E_z$.

$H_y$ for SAMPLE layer           Eq. 5
$F e^{-i(n_s^2 k^2 - \beta^2)^{\frac{1}{2}} x}$ $H_y$ for OVERLAY layer
$C e^{i(n_o^2 k^2 - \beta^2)^{\frac{1}{2}} x} + D e^{-i(n_o^2 k^2 - \beta^2)^{\frac{1}{2}} x}$ $H_y$ for METAL layer
$A e^{i(n_m^2 k^2 - \beta^2)^{\frac{1}{2}} x} + B e^{-i(n_m^2 k^2 - \beta^2)^{\frac{1}{2}} x}$ $H_y$ for CLADDING layer
$E e^{i(n_c^2 k^2 - \beta^2)^{\frac{1}{2}} x}$ $E_z$ for SAMPLE layer           Eq. 6
$(-i/n_s^2 \omega E_0)(-Fi(n_s^2 k^2 - \beta^2)^{\frac{1}{2}} e^{-i(n_s^2 k^2 - \beta^2)^{\frac{1}{2}} x})$ $E_z$ for OVERLAY layer
$(-i/n_o^2 \omega E_0) (Ci(n_o^2 k^2 - \beta^2)^{\frac{1}{2}} e^{i(n_o^2 k^2 - \beta^2)^{\frac{1}{2}} x} -$ $Di(n_o^2 k^2 - \beta^2)^{\frac{1}{2}} e^{-i(n_o^2 k^2 - \beta^2)^{\frac{1}{2}} x})$ $E_z$ for METAL layer
$(-i/n_m^2 \omega E_0)(Ai(n_m^2 k^2 - \beta^2)^{\frac{1}{2}} e^{i(n_m^2 k^2 - \beta^2)^{\frac{1}{2}} x} -$ $Bi(n_m^2 k^2 - \beta^2)^{\frac{1}{2}} e^{-i(n_m^2 k^2 - \beta^2)^{\frac{1}{2}} x})$ -continued $E_z$ for CLADDING layer
$(-i/n_c^2 \omega E_0)(Ei(n_c^2 k^2 - \beta^2)^{\frac{1}{2}} e^{i(n_c^2 k^2 - \beta^2)^{\frac{1}{2}} x})$ where

| | |
|---|---|
| $n_s$ = Sample Index | $\lambda$ = Laser Wavelength |
| $n_o$ = Overlay Index | $k = 2\pi/\lambda$ |
| $n_m$ = Metal Index | $\beta = n_e k$ |
| $n_c$ = Cladding Index | $d_1$ = Silver Thickness |
| $n_e$ = Fiber Effective Index | $d_2$ = Silver Thickness + |
| $t = d_2 - d_1$ (Overlay Thickness). | Overlay Thickness |

The sample and fiber layers contain only one term because the second term would explode as the x-component moved to ±infinity (see FIG. 4).

Boundary conditions dictate that E and H fields must be continuous across a material boundary. Therefore, the $H_y$ and $E_z$ fields in both materials at a layer boundary must be equal. With the following substitutions to simplify the writing of the equations, the $H_y$ and $E_z$ fields are equated across the boundaries according to equations 7-13.

Let $\qquad$ Eq. 7

$\alpha = (\beta^2 - n_s^2 k^2)^{\frac{1}{2}}, \quad \Delta = (\beta^2 - n_m^2 k^2)^{\frac{1}{2}},$ $\rho = (\beta^2 - n_c^2 k^2)^{\frac{1}{2}}, \text{ and } \gamma = (\beta^2 - n_o^2 k^2)^{\frac{1}{2}}.$ $H_y \text{ (at } x = d_2) \; Fe^{-\alpha d_2} = Ce^{\gamma d_2} + De^{-\gamma d_2} \qquad$ Eq. 8

$H_y \text{ (at } x = d_1) \; Ce^{\gamma d_1} + De^{-\gamma d_1} = Ae^{\Delta d_1} + Be^{-\Delta d_1} \qquad$ Eq. 9

$H_y \text{ (at } x = 0) \; A + B = E \qquad$ Eq. 10

$E_x \text{ (at } x = d_2) \; (1/n_s^2)(-F\alpha e^{-\alpha d_2}) = \qquad$ Eq. 11
$(1/n_o^2)(C\gamma e^{\gamma d_2} - D\gamma e^{-\gamma d_2})$ $E_x \text{ (at } x = d_1)(1/n_o^2)(C\gamma e^{\gamma d_1} - D\gamma e^{-\gamma d_1}) = \qquad$ Eq. 12
$(1/n_m^2)(A\Delta e^{\Delta d_1} - B\Delta e^{-\Delta d_1})$ $E_x \text{ (at } x = 0) \; (1/n_m^2)(A\Delta - B\Delta) = (1/n_c^2)(E\rho) \qquad$ Eq. 13

Equations 8-13 are in terms of six unknowns (A-F). The dispersion equation describing the four layer system is obtained by a method similar to that for the three layer system. The six equations are algebraically reduced to two equations and two unknowns whose coefficients are formed into a 2*2 matrix. The determinant of this matrix must equal zero in order for a solution to exist. This solution will indicate the conditions necessary to achieve resonance. The determinant is set equal to zero, then rearranged to solve for $d_2$. The resulting dispersion equation is given by Equation 14.

sample refractive index ($n_s$). Each curve will determine the thickness of the overlay or underlay, based on its refractive index, needed to generate SPR for a given sample index.

Figure 5A:
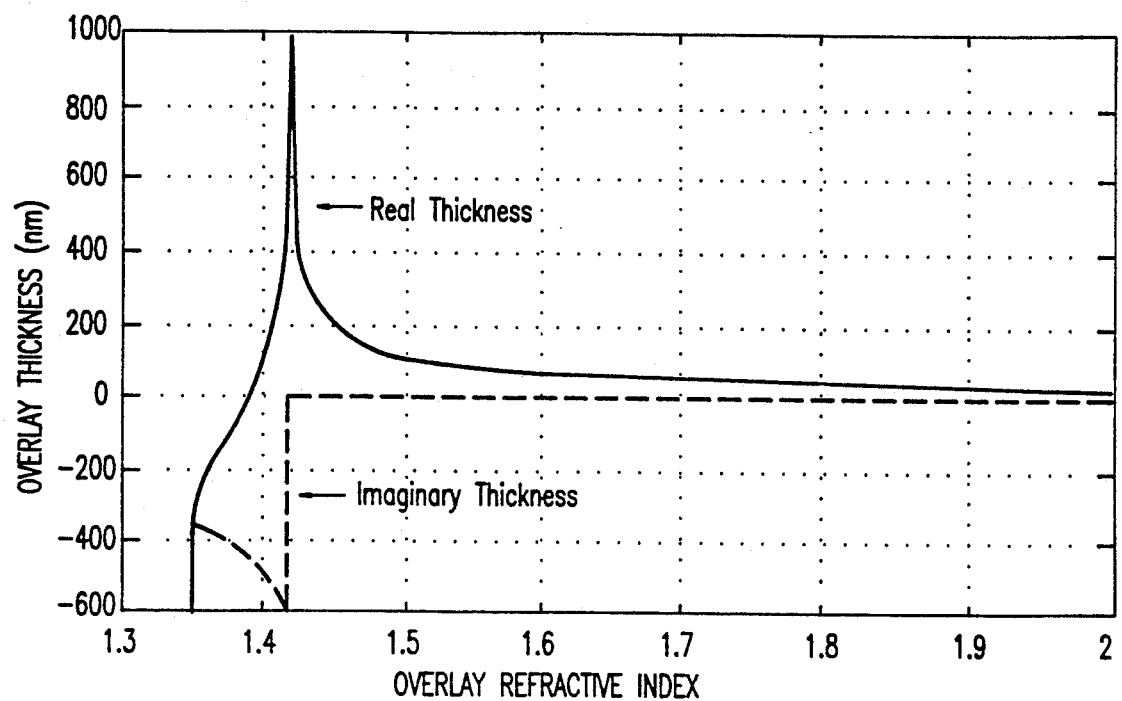
FIGS. 5a and 5b are dispersion plots of overlay thickness versus the overlay refractive index used to determine overlay thickness needed for SPR.
Figure 5B:
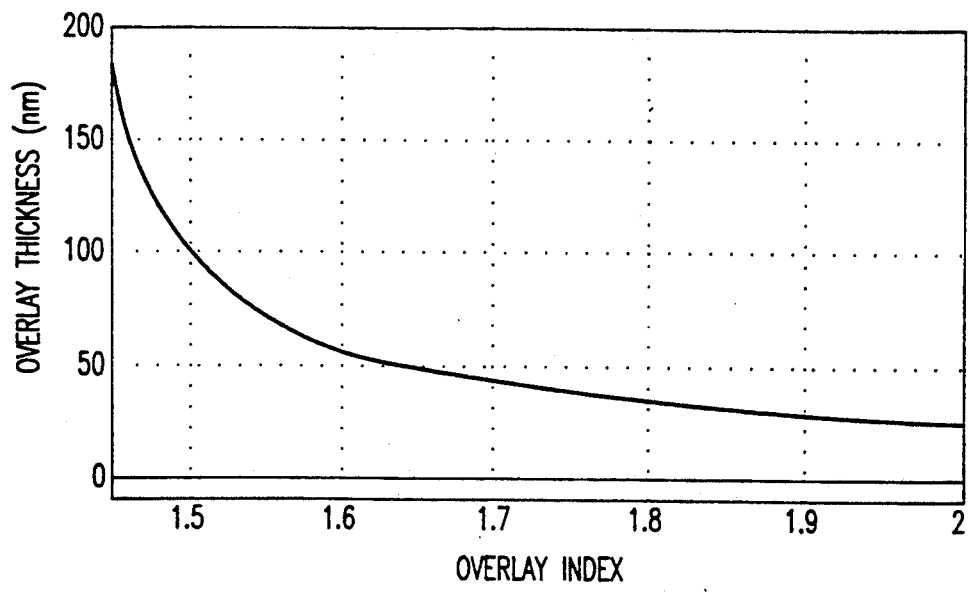

FIGS. 5a and 5b illustrate an example of dispersion plots described above for a quadruple layer system which will employ an overlay material. In generating these plots, the following optical source, metal and fiber were used: a laser diode operating at 780 nm, a 34 nm thick silver metal film, and a Corning Flexcore singlemode (at 780 nm) fiber (Corning Glass Works, Telecom. Div., N.Y.) with a core index of 1.4603, a cladding index of 1.4537, and an effective index of 1.457. Several features of these plots are of interest. First, FIG. 5b shows the plot slopes downward as the overlay refractive index increases. This behavior is expected because less overlay is needed to increase the 'net' index of the sampling region as the refractive index of the overlay increases. Secondly, FIG. 5a shows a sharp, semi-infinite peak at an overlay index of 1.419. This index exactly matches the experimentally determined and theoretically predicted sample index needed to generate SPR on this system if no overlay were present. With reference back to FIG. 5b, it can be seen that a thickness of 100 nm of an overlay material with a refractive index of 1.5 will be needed to generate SPR. With refrence to FIG. 5a, it can be seen that at overlay refractive indices less than 1.419 the thickness contains an imaginary component. This can be interpreted as a region of operation that requires an overlay material with a complex index of refraction, such as a metal. For dielectric overlay materials the region of $n_o > 1.419$ is considered as the functioning range of this sensor.

EXAMPLE 3—EXPERIMENTAL CONFIGURATION AND RESULTS

Figure 6:
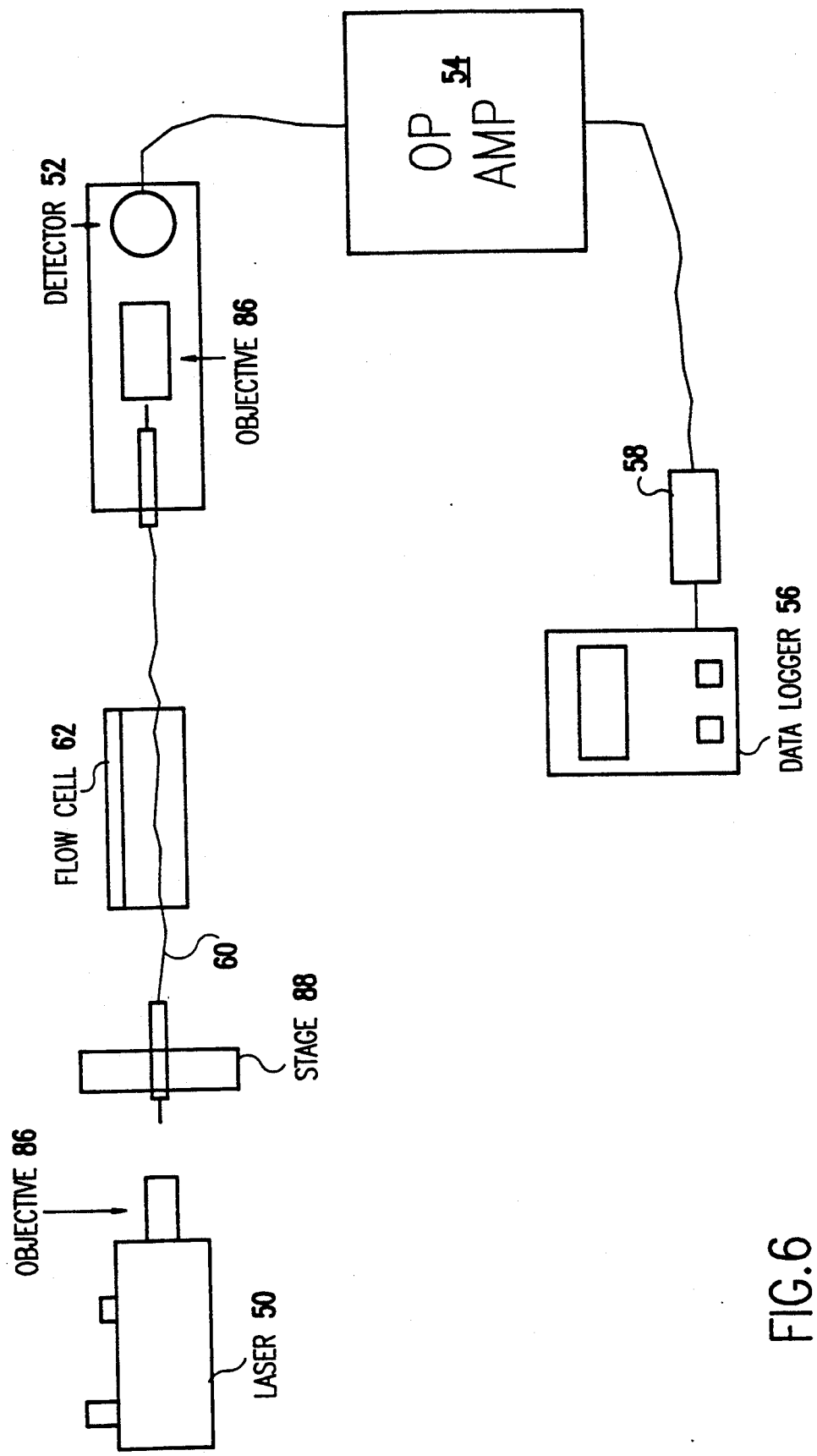
FIG. 6 is a schematic drawing of an on-line experimental optical fiber-based SPR sensor system according to the present invention.

FIG. 6 shows the experimental testing arrangement for the optical fiber SPR sensor of the present invention. A source of coherent radiation, such as a laser 50, is used as the source of light, and a suitable photosensitive device is used as the optical detector 52. The output of the optical detector 52 is routed through an operational amplifier 54 and collected by a data logger 56. Output from the operational amplifier 54 may be routed through an analog to digital converter 58. For testing purposes, the sensing portion of the fiber 60 is contained in a 2 ml sample volume plexiglass flow cell 62.

Figure 7:
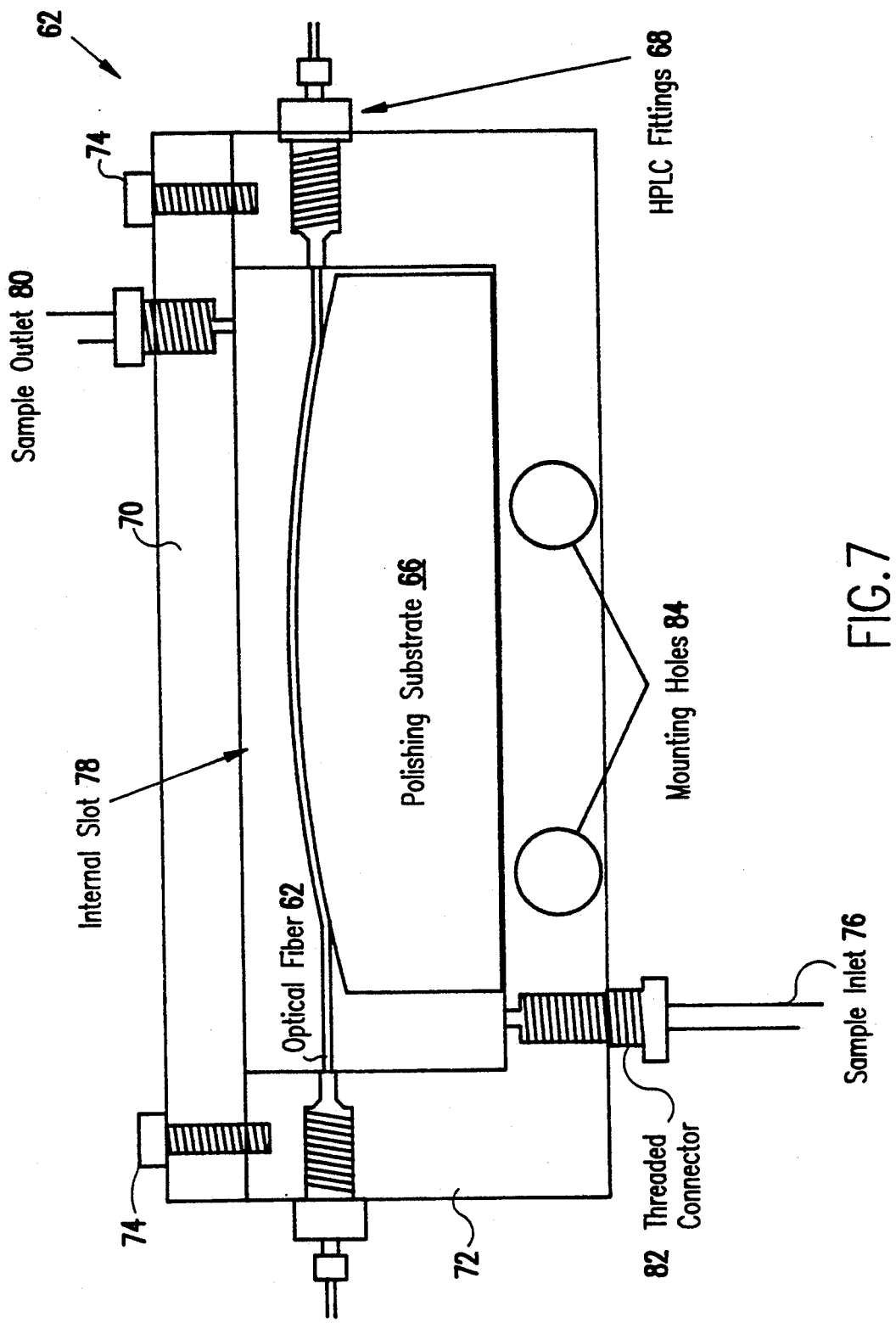
FIG. 7 is a schematic drawing of a flow cell used in the experimental system of FIG. 6.

FIG. 7 shows the 2 ml plexiglass flow cell 62 is comprised of a top 70 secured to a bottom portion 72 by screws 74. The optical fiber 60 passes through the bottom portion 74 and is positioned on the curved polishing substrate 66. High performance liquid chromotography (HPLC) fittings 68 can be positioned around the optical fiber 60 to seal th flow cell 62. The fluid of interest passes through tubing into the sample inlet 76, $$d_2 = \ln\left( \frac{[\Delta/n_m^2 + \rho/n_c^2][e^{(\gamma+\Delta)d_1}][\gamma/n_o^2 - \Delta/n_m^2] - [\rho/n_c^2 - \Delta/n_m^2][e^{(\gamma-\Delta)d_1}][\gamma/n_o^2 + \Delta/n_m^2]}{[\rho/n_c^2 - \Delta/n_m^2][e^{-(\gamma+\Delta)d_1}][Y][\Delta/n_m^2 - \gamma/n_o^2] + [\Delta/n_m^2 + \rho/n_c^2][e^{(\Delta-\gamma)d_1}][Y][\gamma/n_o^2 + \Delta/n_m^2]} \right)/2\gamma \qquad \text{Eq. 14}$$

where $Y = [(\gamma/n_o^2) + (\alpha/n_s^2)]/[(\gamma/n_o^2) - (\alpha/n_s^2)].$ $\qquad$ Eq. 15

Upon selection of a fiber, optical source and metal, all of the parameters are fixed except for $n_s$, $n_o$, and t. Equation 14 is plotted for the overlay or underlay thickness (t) as a function of the overlay index ($n_o$), and a family of curves results. Each curve represents a different fills the internal volume (internal slot 78), and then passes out through tubing at sample outlet 80. Threaded connectors 82 can be used to seal the flow cell 62 and mounting holes 84 can be used to secure the flow cell 62 to a support structure.

While FIGS. 6 and 7 show the use of a flow cell 62, it should be understood that other on-line configurations could be employed, as well as batch process dipping arrangements, for bringing the sample into contact with the optical fiber 62. Objective lenses 86 and a stage 88 can be used for focussing the radiation source 50 on the detector 52.

Figure 8:
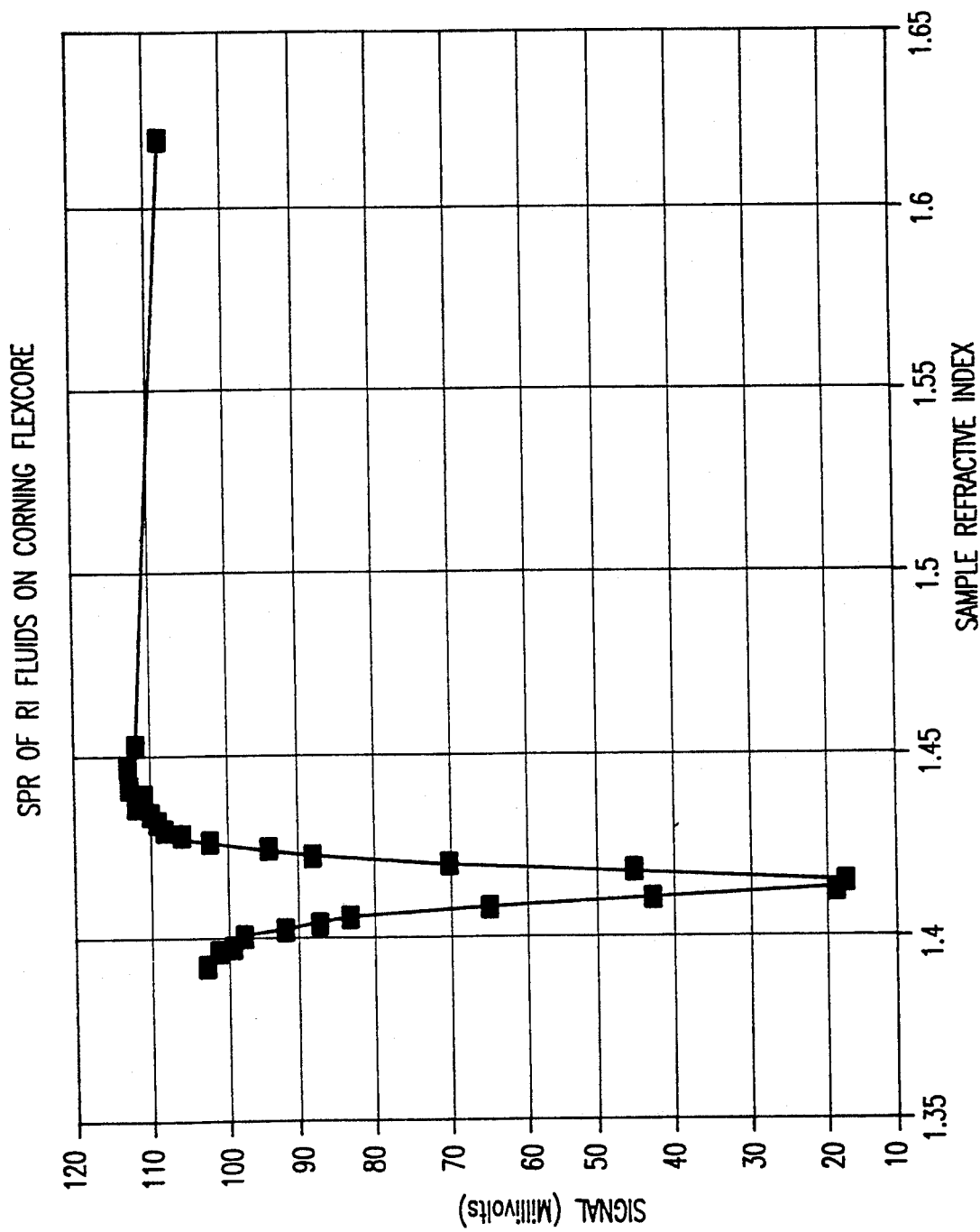
FIG. 8 is a graph showing the SPR of standardized fluids having a known refractive index on a fiber with a metal film coating, but no overlay or underlay material coating.

In the experiments, one fiber was coated with 35 nm of silver by vacuum deposition, but received no overlay material. The fiber was a Corning Flexcore single-mode fiber as described above. The fiber was placed in the instrumentation shown in FIGS. 6 and 7 and tested by successive applications of Cargille (Cargille Labs., N.J. 07009) refractive index matching fluids to its sensing area. After each fluid application, the fiber was rinsed with cyclohexane to clean the silver surface. The dispersion equations in Johnstone, supra, indicate that a sample index of 1.4197 should promote plasmon resonance. Data presented in FIG. 8 shows a surface plasmon resonance signal minimum at a sample refractive index of 1.419. This refractive index value exactly matches the sharp peak in the four-layer dispersion equation described herein above.

Figure 9:
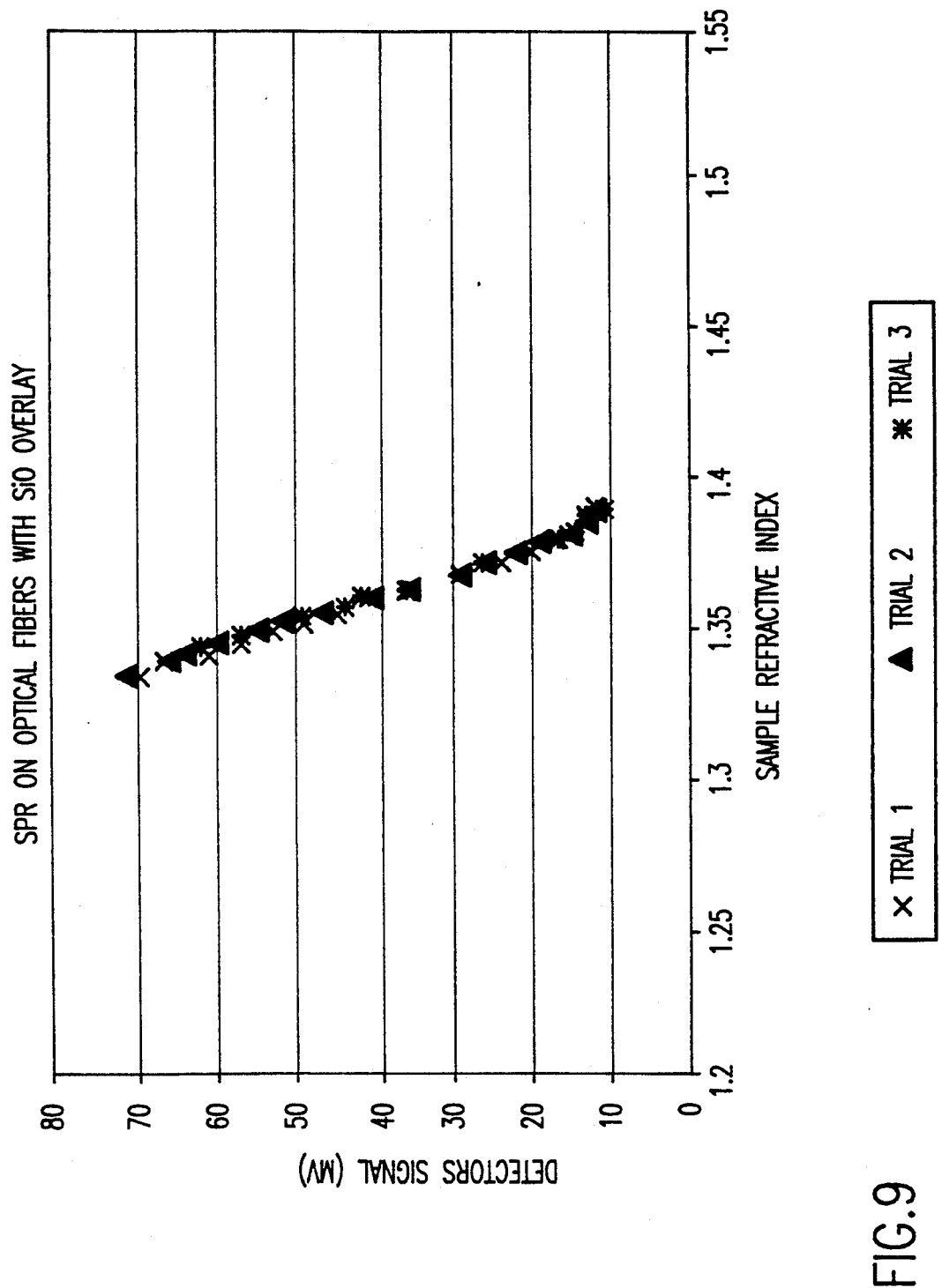
FIG. 9 is a graph showing the SPR of standardized fluids having a known refractive index on a fiber with a silver coating and an silicon monoxide overlay coating where the thickness of the silicon monoxide overlay has been optimized.

In the experiments, another fiber (Corning Flexcore single-mode fiber) was overcoated with silicon monoxide (SiO) as a test overlay material. Silicon monoxide has a relatively high refractive index (1.928 at 780 nm), has a melting point (approximately 1700° C.) that allows it to be easily vapor deposited, and is insoluble in water. However, it should be understood that the overlay could be any of a number of materials including, but not limited to dielectrics, glasses, metals, metal oxides, chalcogenides, semiconductors, organic films, polymeric materials, and the like. For testing, equation 14 was solved for $\lambda=780$ nm, $n_o=1.928$, $n_m=5.5i$ (silver), $d_1=34$ nm (silver thickness), and Corning Flexcore single-mode fiber, for a sample index of 1.350. The results indicated that 27.4 nm of SiO would be needed to generate SPR under the given conditions. Vacuum deposition was carried out with the application of 33.7 nm of silver and 27.8 nm of silicon monoxide overlay. The fiber was then placed in the instrument and solutions of sucrose in water having standardized refractive indices were applied. The experiment was repeated a total of three times and the data is shown in FIG. 9. The dispersion equation accurately predicted (within 3%) the results obtained from the optical fiber-based SPR sensor. The resonance condition occurred well below the 1.42 sample index achieved with no overlay, and the results were very repeatable over the three trials.

Figure 10:
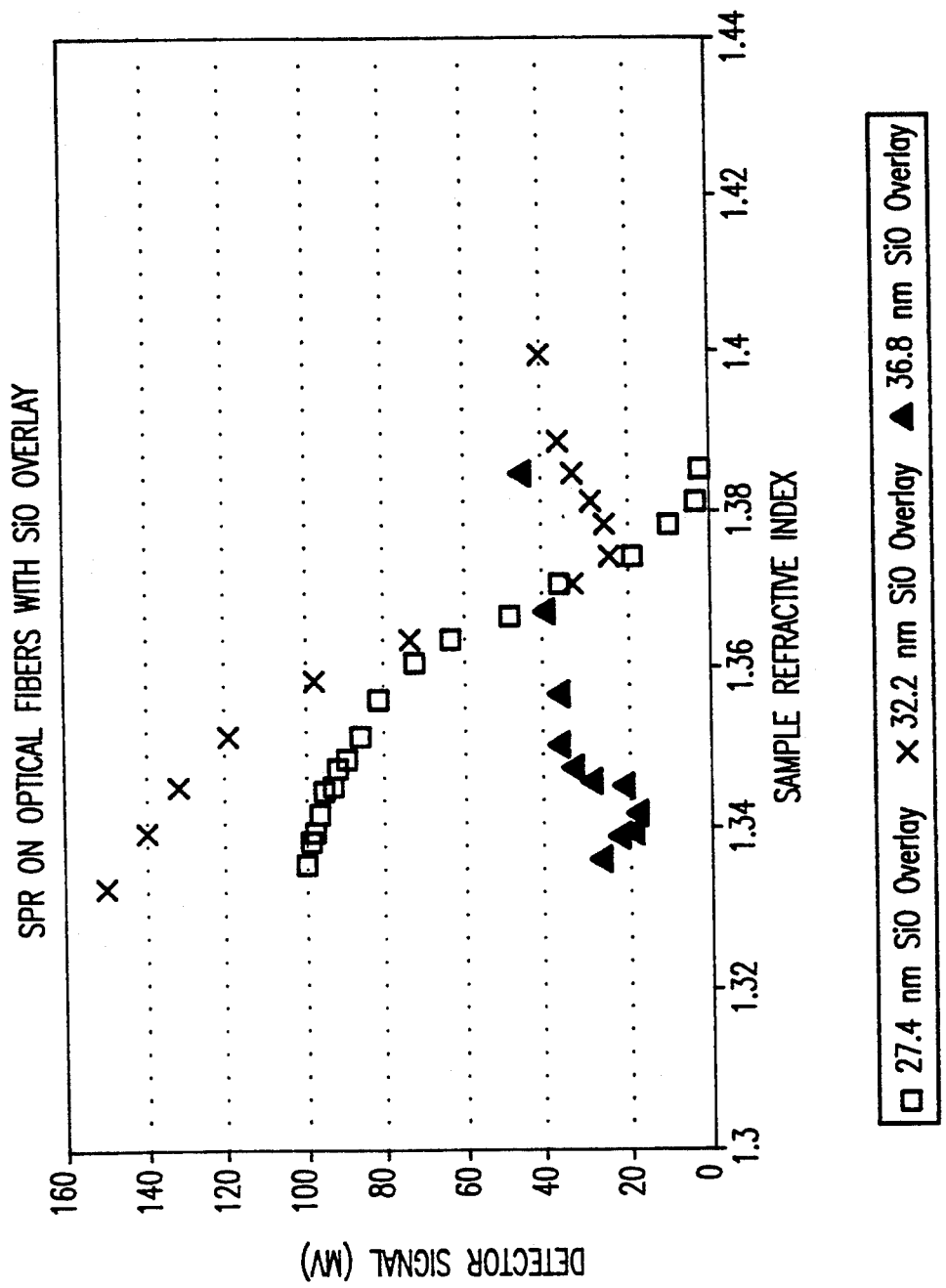
FIG. 10 is a graph showing the SPR of standardized fluids having a known refractive index on fibers with a silver coating and a silicon monoxide overlay coating where the thickness of the silicon monoxide layer varies.

A similar trial was then carried out on polished optical fibers with 34 nm of silver films and SiO overlay material where the thickness of the SiO overlay was varied for each fiber (e.g., 27.4 nm, 32.2 nm, and 36.8 nm). The results, shown in FIG. 10, indicate that the sample index generating resonance decreases with increasing overlay thickness. This behavior matches that predicted by the dispersion relationship.

Other modifications of the sensor are possible to increase the scope of its applications. These include, but are not limited to, the use of elliptical core polarization maintaining fibers, polarizing optical fibers that transmit only one polarization state, i.e. TM, while attenuating the other, i.e., TE, the use of a dual-fiber geometry or a multimode fiber to allow a reference arm, the use of planar waveguides in place of the optical fiber, microscaling of the device with integrated optical components, remote sensing with long range optical cables, and the use of disposable sensing elements.

Certain applications of the device of the present invention are now illustrated by Example.

EXAMPLE 4—BIOLOGICAL AND BIOCHEMICAL APPLICATIONS

Figure 11:
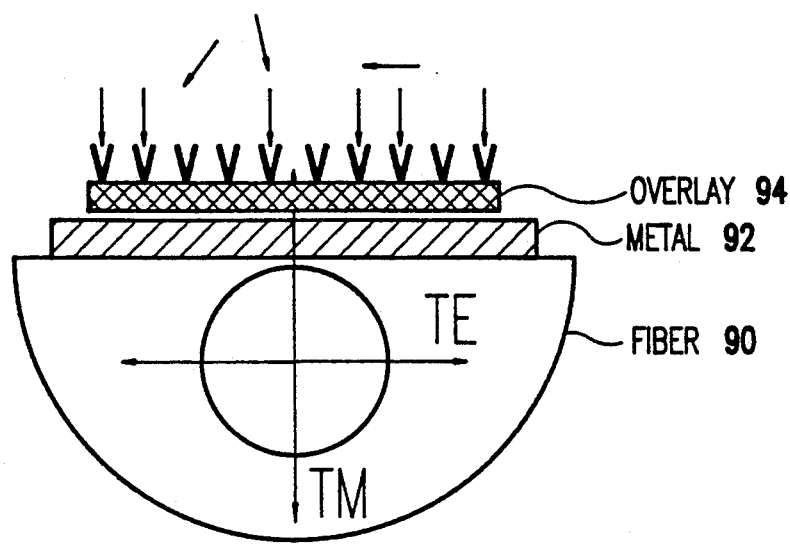
FIG. 11 is a cross-sectional view of an optical fiber-based SPR sensor according to the present invention arranged for monitoring biological interactions.

An important application of this sensor is in the area of biological and biochemical analyses. FIG. 11 shows a biosensor design in accordance with the present invention. The optical fiber 90 has a metal film 92 and an overlay 94 material as described above. In addition, immobilized antigen 96 is bound to the surface of the overlay 94. Antibody 98 in a sample fluid becomes bound to the immobilized antigen 96, thereby changing the refractive index of the overlay 94, and thus allowing the presence of an antibody 98 in the sample fluid to be detected. While the solid-phase has been described above as an immobilized antigen, the solid-phase can be varied to suit the needs of the user and can include either antigens or antibodies or other receptors or portions thereof including: $F_{ab}$ fragments, hypervariable fragments, single chain antigen binding proteins, and the like. The optical fiber-based SPR biosensor of FIG. 11 is very sensistive to refractive index (R.I.) changes, such as those that occur in a bioreaction (e.g., the reaction between antibody & antigen, enzyme & substrate, cell & receptor, and the like). The R.I. may range from about 1.0 to 1.5. The sensor would have its active area coated with one half of a reaction pair (e.g., an antigen, antibody, etc.). Reactions with the other half of the reaction pair found in a biological sample of interest will cause a change in R.I. which will be monitored as a change in optical throughput in the fiber.

The optical fiber-based SPR bioligical sensor has several advantages over more traditional assay techniques, such as ELISA. It requires only one step, viz., the addition of the sample to be analyzed. It requires no complex reaction and washing steps, no radioactive or fluorescent tags, and no expensive equipment to measure those markers.

In addition, the optical fiber-based SPR biological sensor of the present invention has several advantages over prior art prism and glass rod sensors. For example, the SPR biological sensor of the present invention requires no moving parts, has a very simple sample introduction mechanism, requires no angle measurements, and does not require expensive and complex detectors (e.g., photodiode arrays, charge coupled displays (CCD), etc.). Furthermore, the SPR biological sensor of the present invention can employ disposable fiber sensing elements that do not require fitting in sensor blocks, and has excellent microscaling potential. Lastly, it is extremely inexpensive and simple to produce sensing elements for the SPR biological sensor of the present invention.

EXAMPLE 5—CORROSION MONITORING APPLICATIONS

Corrosion is a critical problem in many applications and has particular relevance in the aerospace and shipbuilding industries. There is currently no simple and accurate method for the detection of corrosion in metallic parts on aircraft and ships.

Figure 12:
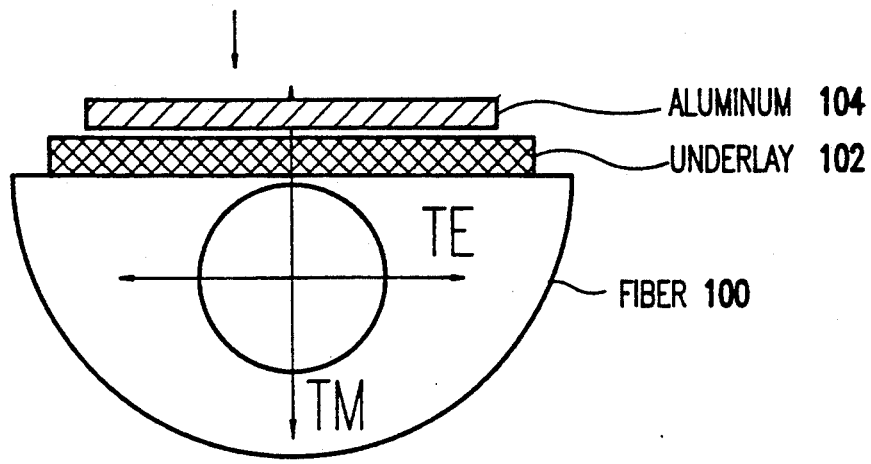
FIG. 12 is a cross-sectional view of an optical fiber-based SPR sensor according to the present invention arranged to monitor aluminum corrosion.

FIG. 12 shows a corrosion monitor in accordance with the present invention arranged to monitor aluminum corrosion; however, it should be understood that corrosion of other metals could be similarly monitored. In one embodiment, a fiber 100 can be embedded in a part to be monitored. At the site to be monitored, the fiber 100 will have an underlayer 102 of silicon monoxide or other suitable dielectric material. The aluminum 104 surface of the part at the site to be monitored will serve as the metal film. Corrosive agents 106, such as salt water, etc., will change the surface characteristics (e.g., thickness and refractive index) of the aluminum 104; thereby, causing a change in SPR which will be detected by the optical fiber-based SPR sensor of the present invention. In another embodiment where the optical fiber-based SPR sensor of FIG. 12 is not embedded in the part, but is placed adjacent the parts to be monitored, a technician will be alerted to inspect the parts in the immediate vicinity of the optical fiber-based SPR sensor for replacement or repair, etc.

The optical fiber-based SPR sensor could be multiplexed or arrayed to cover an entire aircraft or ship at low expense with very little added weight. This would enable the technician to look for corrosion only in those areas where the sensor indicates corrosion problem. It is also small enough to be placed in hard-to-reach areas.

Of course, the optical fiber-based SPR corrosion sensor could be used in many other applications where corrosion monitoring is necessary. While FIG. 12 shows the use of an underlayer 102, it should be understood that a porous overlayer could be used instead where the corrosive agents 106 are free to penetrate the overlayer.

EXAMPLE 6—PROCESS CONTROL APPLICATIONS

Figure 13:
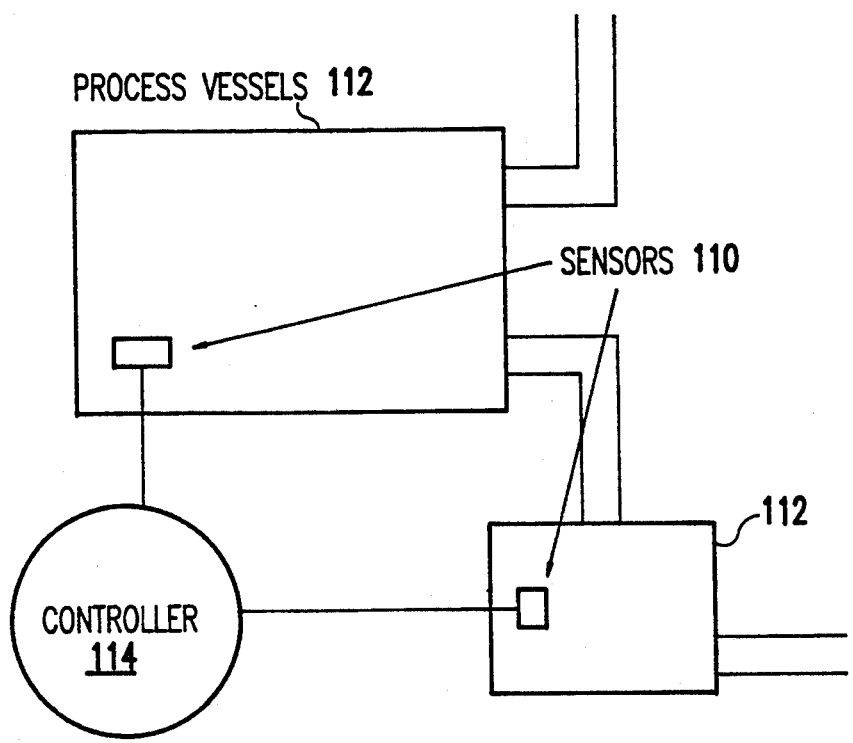
FIG. 13 is a schematic drawing showing the optical fiber based SPR sensors of the present invention used in process control.

FIG. 13 shows that the optical fiber-based SPR sensors of the present invention can be used to monitor chemical and biochemical processes. As a chemical reaction or process proceeds, it will usually undergo a change in refractive index. The SPR sensors of the present invention can be used to monitor a change in refractive index as a function of change in optical throughput intensity. FIG. 13 shows optical fiber-based SPR sensors 110 positioned in separate process vessels 112. Since the optical fiber-based SPR sensors are small, inexpensive, and disposable, they can be arrayed throughout a complex multi-step process and tied into the computer control system 114 which regulates the process. In a particular embodiment, the sensors 110 can be configured such that the media at the endpoint of a reaction or process has a refractive index which will cause SPR to be generated. Hence, the endpoint can easily be detected by measuring changes in optical throughput in the fibers of sensors 110. The sensors 110 could be customized to the specific process and constructed of materials that survive harsh chemical environments. It must be noted that the device is sensitive to any change in refractive index and would be subject to interference caused by changes in refractive index of impurities or spectator molecules in the process stream. Hence, in another particular embodiment, the SPR sensors could be fabricated to detect the presence of particular impurities in a process stream.

EXAMPLE 7—CHROMATOGRAPHY APPLICATIONS

Changes in refractive index are commonly used in liquid chromotography and HPLC as an indicator that a particular reaction has occurred or a particular compound of interest is present in solution. A small volume flow cell, with an optical window, attached to the end of the column is typically used to refract a narrow light beam passing through the effluent contained in the cell. The refraction is related to the effluent's refractive index.

Figure 14:
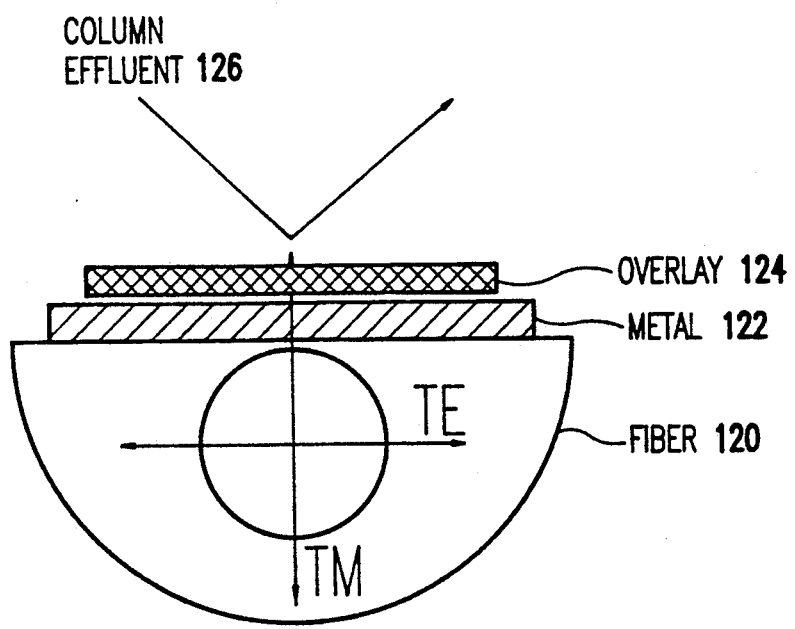
FIG. 14 is a cross-sectional view of an optical fiber-based SPR sensor arranged for monitoring column effluent so that it may perform as a chromatography detector.

FIG. 14 shows an optical fiber-based SPR sensor which has been microscaled to fit into the output end of the HPLC column. The optical fiber 120 has a metal film 122 and overlay 124 material optimized so that the mobile phase's refractive index (column effluent 126) generates the surface plasmon resonance condition. Specifically, the refractive index of the column effluent 26 should fall on the steep part of the resonance curve so that changes in refractive index due to the presence of solutes would cause large changes in throughput in the SPR fiber sensor.

The optical fiber-based sensor of the present invention is so small that it could be placed directly into the end of the HPLC column, eliminating the need and problems associated with current flow cell designs.

As with other refractive index sensing devices, the optical fiber-based SPR sensors of this invention will be somewhat sensitive to temperature fluctuations. A temperature control or compensation system may be needed if very sensitive measurements are to be carried out. This could involve one or more of the following: providing a temperature controlled enclosure, using an elliptical core optical fiber or some other device to yield a reference arm, or experimentally determining a temperature correction factor. The signal/noise ratio of the optical fiber-based SPR sensors of this invention are fairly good; therefore, temperature fluctuations should only be a problem if the temperature change is significant or if a very sensitive (small change in refractive index) reaction is to be monitored.

Apart from the features described above, certain other aspects of the invention are noteworthy.

Figure 15A:
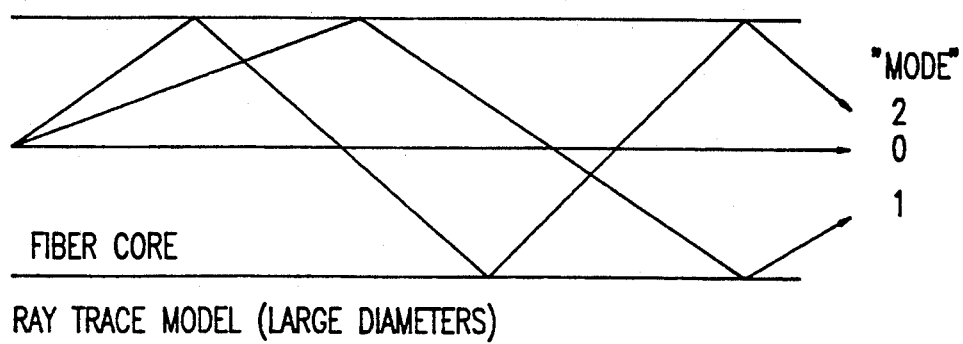
FIGS. 15a and 15b are graphs showing the ray trace model of propogation in large diameter fiber cores and the mode model of propogation in small diameter fiber cores, respectively.
Figure 15B:
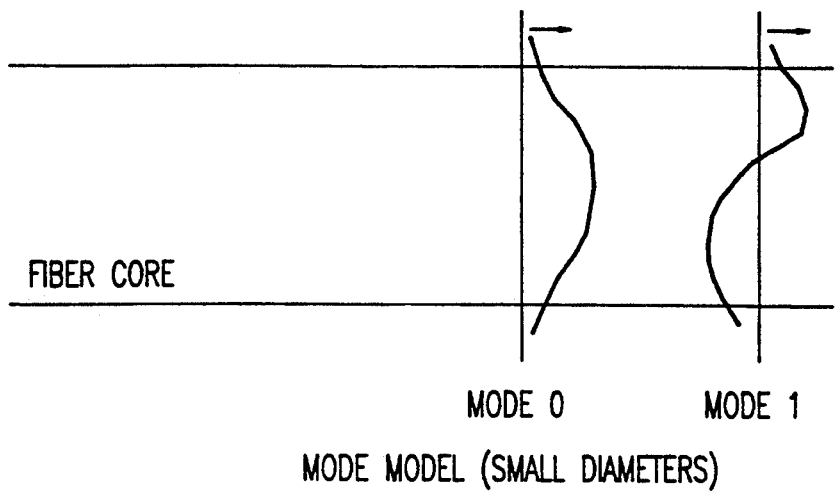

First, it may be pointed out that at the fiber diameters below about 50–100 microns which certain embodiments of the present invention may employ, the ray trace analysis of light progression in a fiber core shown in FIG. 15a no longer holds. At these micro dimensions, the quantum nature of light takes effect and the propagation of light in the fiber must be described in mode theory and not in terms of ray trace analysis. A mode is a description of the lateral optical field distribution in the fiber, and the number of modes supported by a fiber depends on the fiber's core and cladding indices of refraction, the core diameter, and the wavelength. Each mode is a discrete solution to Maxwell's equations as applied to the waveguide. Even though a fiber may contain many modes, it is impossible to adequately spatially separate these modes at the distal terminus of a small diameter fiber because they travel through the fiber together. For instance, a device such as described in U.S. Pat. No. 5,047,213 to Finlan, cannot work below "rod" diameters of about 50 microns, depending on the wavelength, because it is impossible to spatially separate the rays (modes) after they exit the fiber.

The optical fiber-based SPR sensor of the present invention is an intrinsic sensor wherein the fiber itself plays a crucial role in the sensing mechanism. The field distributions in the sensor are strongly dependent on the fiber parameters (e.g., core index, cladding index, core diameter) which play an important role in the mathematical description of the surface plasmon effect on the fiber. The fiber is not simply a light delivery system to a prism-like sensor which is what the extrinsic sensors do (e.g., Finlan, supra) wherein a large number of rays (modes) are simultaneously monitored with a complex detection device, such as a photodiode array or CCD imager. Such devices have a large numerical aperture and V number. In contrast, the optical fiber-based SPR sensor of the present invention uses a single mode fiber and the intensity of that mode is greatly affected by the plasmon conditions. The output of the sensor of the present invention can be monitored with a very simple and inexpensive photodiode and can have a small numerical aperture and a V number below 2.405.

Additionally, the sensor of the present invention uses a polarized radiation source which can easily interact with the plasmon on the metal-coated fiber. Surface plasmon is a polarization specific phenomenon. Only light with an electric field oriented perpendicular to the metal surface can couple to the plasmon. This is called the transverse magnetic or TM polarization. Since the inventive device operates in a single mode fashion, the fiber can be curved to accomodate a particular application. Single mode devices are relatively insensitive to bending. The device can also use polarization maintaining fibers, such as elliptical core fibers. This type of fiber maintains the two polarizations in the core over long distances. One polarization (TM) could be used to interact with the plasmon, while the other (transverse electric or TE) could be used as a reference arm. The two polarizations can be separated with a Wollaston prism after exiting the fiber. Furthermore, since the fiber sensor of the present invention is single mode, it is insensitive to radiation (e.g.laser) launch angle, and polishing angle is not important as long as the polish is fairly parallel to the fiber core, and the polished surface is perpendicular to the laser's plane of polarization.

A particular advantage of this sensor is its small diameter fiber that could easily be nonintrusively embedded into structures for analysis, such as corrosion monitoring. Since the device is all-fiber, it could be used for remote sensing, where the laser and detector are housed remotely from the sensing element. Since the device has only a surface modified optical fiber, it could be easily microscaled with little manufacturing. It is also possible to have more than one sensing element on a single fiber strand. Moreover, the sensing element could be used in any fiber optic network, such as multiple sensors arranged in a multiplexed, networked, parallel, or series fashion. The sensor could also be employed in a fiber optic coupler where the sensor functions as an arm of the coupler. The sensor could also be spliced into an optical fiber line in order to make the sensor disposable or remote.

It is understood that the examples and embodiments described herein are for illustrative purposes only and that various modifications or changes in light thereof will be suggested to persons skilled in the art and are to be included within the spirit and purview of this application and scope of the appended claims.

Having thus described our invention, what we claim as new and desire to secure by Letters Patent is as follows:

1. A surface plasmon resonance sensor, comprising:
   an optical fiber;
   a source of electromagnetic radiation connected to said optical fiber;
   first and second films coated on each other and on said optical fiber at a sample contacting region of said optical fiber, said first and second films having a combined thickness small enough to allow an evanescent field portion of a beam of electromagnetic radiation supplied from said source into said optical fiber to penetrate into both said first and second films; and
   a detector connected to said optical fiber for detecting surface plasmon resonance as a function of a thickness and refractive index for both said first and second films and a refractive index of said sample.

2. The surface plasmon resonance sensor of claim 1 further comprising a means for conveying said sample to said sample contacting region of said optical fiber.

3. The surface plasmon resonance sensor of claim 3 wherein said means for conveying includes a flow cell housing said optical fiber.

4. The surface plasmon resonance sensor of claim 1 wherein said first film is selected from the group consisting of silver, gold, chromium, silicon, germanium, and alloys and oxides thereof.

5. The surface plasmon resonance sensor of claim 1, wherein said second film is selected from the group consisting of dielectric materials, polymeric materials, metals, metal oxides, chalcogenides, semiconductors, organic layers, inorganic layers, and glass materials.

6. The surface plasmon resonance sensor of claim 1 wherein said source of electromagnetic radiation is a laser.

7. The surface plasmon resonance sensor of claim 1 further comprising a means to identify changes in surface plasmon resonance.

8. The surface plasmon resonance sensor of claim 1 wherein said optical fiber is a single mode optical fiber.

9. The surface plasmon resonance sensor of claim 1 wherein said first film is a metal or metal alloy and said second film is silicon monoxide.

10. The surface plasmon resonance sensor of claim 1 wherein said optical fiber is less than fifty microns in diameter.

11. The surface plasmon resonance sensor of claim 1 wherein said detector can detect surface plasmon resonance when said sample has a refractive index ranging between 1.00 and 1.39.

12. The surface plasmon resonance sensor of claim 1 wherein said detector can detect surface plasmon resonance when said sample has a refractive index ranging between 1.00 and 1.50.

13. The surface plasmon resonance sensor of claim 1
   wherein said first film is selected from the group consisting of silver, gold, chromium, silicon, germanium, and alloys and oxides thereof,
   wherein said second film is selected from the group consisting of dielectric materials, polymeric materials, metals, metal oxides, chalcogenides, semiconductors, organic layers, inorganic layers, and glass materials, and
   wherein said second film overlies said first film.

14. The surface plasmon sensor of claim 13 wherein said second film is porous.

15. The surface plasmon sensor of claim 13 further comprising a biomaterial specific for binding an analyte of interest in said sample immobilized on said second film.

16. The surface plasmon resonance sensor of claim 1
   wherein said first film is selected from the group consisting of silver, gold, chromium, silicon, germanium, and alloys and oxides thereof,
   wherein said second film is selected from the group consisting of dielectric materials, polymeric materials, metals, metal oxides, chalcogenides, semiconductors, organic layers, inorganic layers, and glass materials, and wherein said second film underlies said first film.

17. The surface plasmon sensor of claim 1 wherein said second film comprises two or more materials selected from the group consisting of dielectric materials, polymeric materials, metals, metal oxides, chalcogenides, semiconductors, organic layers, inorganic layers, and glass materials.

18. A surface plasmon resonance sensor, comprising:
an optical waveguide;
a source of electromagnetic radiation connected to said optical waveguide;
first and second films coated on each other and on said optical waveguide at a sample contacting region of said optical waveguide, said first and second films having a combined thickness small enough to allow an evanescent field portion of a beam of electromagnetic radiation supplied from said source into said optical waveguide to penetrate into both said first and second films; and
a detector connected to said optical waveguide for detecting surface plasmon resonance as a function of a thickness and refractive index for both said first and second films and a refractive index of said sample.

19. A biochemical or biological sensor, comprising:
an optical fiber;
a source of electromagnetic radiation connected to said optical fiber;
first and second films coated on each other and on said optical fiber at a sample contacting region of said optical fiber, said first and second films having a combined thickness small enough to allow an evanescent field portion of a beam of electromagnetic radiation supplied from said source into said optical fiber to penetrate into both said first and second films, said first film being a metal or metal alloy film, said second film being selected from the group consisting of dielectric materials, polymeric materials, metals, metal oxides, chalcogenides, semiconductors, organic layers, inorganic layers, and glass materials, said first film being coated on said sample contacting region of said optical fiber and said second film being coated on top of said first film;
a biomaterial specific for binding an analyte of interest in a sample immobilized on said second film; and
a detector connected to said optical fiber for detecting changes in surface plasmon resonance which occur when said biomaterial binds said analyte of interest in said sample as a function of a thickness and refractive index for both said first and second films.

20. A corrosion sensor, comprising:
an optical fiber;
a source of electromagnetic radiation connected to said optical fiber;
first and second films coated on each other and on said optical fiber at a sample contacting region of said optical fiber, said first and second films having a combined thickness small enough to allow an evanescent field portion of a beam of electromagnetic radiation supplied from said source into said optical fiber to penetrate into both said first and second films, said first film being a metal or metal alloy;
a detector connected to said optical fiber for detecting changes in surface plasmon resonance when said metal or metal alloy in said first film corrodes due to exposure to corrosive agents in a sample which contacts said first film, said changes in surface plasmon resonance being a function of a thickness and refractive index for both said first and second films.

21. A corrosion sensor as recited in claim 20 wherein said second film is porous and allows said sample to permeate therethrough to contact said first film.

22. A surface plasmon resonance sensor for monitoring effluent from a liquid chromatography or high performance liquid chromotography column, comprising:
an optical fiber;
a source of electromagnetic radiation connected to said optical fiber;
first and second films coated on each other and on said optical fiber at a sample contacting region of said optical fiber, said first and second films having a combined thickness small enough to allow an evanescent field portion of a beam of electromagnetic radiation supplied from said source into said optical fiber to penetrate into both said first and second films;
means to convey effluent from a liquid chromatography or high performance liquid chromatography column over said sample contacting region of said optical fiber; and
a detector connected to said optical fiber for detecting surface plasmon resonance as a function of a thickness and refractive index for both said first and second films and a refractive index of said effluent.

* * * * *